(12) United States Patent
Fujimori

(10) Patent No.: US 8,123,677 B2
(45) Date of Patent: Feb. 28, 2012

(54) BODY-INSERTABLE APPARATUS

(75) Inventor: Noriyuki Fujimori, Nagano (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1086 days.

(21) Appl. No.: 11/953,268

(22) Filed: Dec. 10, 2007

(65) Prior Publication Data

US 2008/0139882 A1   Jun. 12, 2008

(30) Foreign Application Priority Data

Dec. 12, 2006   (JP) ................................. 2006-334823

(51) Int. Cl.
*A61B 1/00*   (2006.01)
(52) U.S. Cl. .................... 600/118; 600/160; 600/130
(58) Field of Classification Search .................. 600/101, 600/109, 118, 160, 130
See application file for complete search history.

(56) References Cited

U.S. PATENT DOCUMENTS

| | | | |
|---|---|---|---|
| 2002/0109774 A1 | 8/2002 | Meron et al. | |
| 2005/0171398 A1 | 8/2005 | Khait et al. | |
| 2006/0004255 A1 | 1/2006 | Iddan et al. | |
| 2006/0241422 A1* | 10/2006 | Muratayev et al. | 600/435 |
| 2006/0264709 A1* | 11/2006 | Fujimori et al. | 600/130 |
| 2007/0118012 A1* | 5/2007 | Gilad | 600/109 |
| 2007/0129602 A1* | 6/2007 | Bettesh et al. | 600/118 |

FOREIGN PATENT DOCUMENTS

| | | |
|---|---|---|
| EP | 1 702 553 A1 | 9/2006 |
| JP | 2001-112740 | 4/2001 |
| JP | 2003-019111 | 1/2003 |
| JP | 2003-325441 A | 11/2003 |
| JP | 2006-020853 A | 1/2006 |
| JP | 2006-141897 | 6/2006 |
| JP | 2006-297080 | 11/2006 |
| WO | WO 02/054932 A2 | 7/2002 |
| WO | WO 2004/028335 A2 | 4/2004 |
| WO | WO 2004/059568 A1 | 7/2004 |

OTHER PUBLICATIONS

European Office Action dated Oct. 15, 2010.
Extended Supplementary European Search Report dated Oct. 29, 2009.
Japanese Office Action dated Sep. 20, 2011 from corresponding Japanese Patent Application No. 2006-334823 together with English language translation.

* cited by examiner

*Primary Examiner* — John P Leubecker
*Assistant Examiner* — Christopher Sponheimer
(74) *Attorney, Agent, or Firm* — Scully, Scott, Murphy & Presser, P.C.

(57) ABSTRACT

A body-insertable apparatus including a capsule-like casing, an illuminating unit, an imaging unit, and an antenna is provided. The capsule-like casing is formed in a capsule-like shape and includes a transparent imaging dome. The illuminating unit is arranged in the capsule-like casing and illuminates an examined site of a subject through the imaging dome. The imaging unit is arranged in the capsule-like casing and takes an image of the examined site illuminated by the illuminating unit. The antenna is arranged in the imaging dome at a position outside an imaging field of view of the imaging dome to transmit image information obtained through imaging by the imaging unit to an outside of the subject.

10 Claims, 7 Drawing Sheets

BODY-INSERTABLE APPARATUS

CROSS-REFERENCE TO RELATED APPLICATIONS

This application is based upon and claims the benefit of priority from Japanese Patent Application No. 2006-334823, filed Dec. 12, 2006, the entire contents of which are incorporated herein by reference.

BACKGROUND OF THE INVENTION

1. Field of the Invention

The present invention relates to a body-insertable apparatus which is inserted into a subject to take an image of an examined site and to output the image by radio to an outside of the subject.

2. Description of the Related Art

In recent years, a swallowable capsule endoscope has been developed in the field of endoscope. The capsule endoscope is equipped with an imaging function and a radio function as described in Japanese Patent Application Laid-Open No. 2003-19111, for example. After being swallowed from the mouth of a patient for an observation of an interior of a body cavity, the capsule endoscope travels through internal organs such as an esophagus, a stomach, and a small intestine, following peristaltic movements thereof to sequentially perform imaging until naturally excreted from the body of the patient.

While the capsule endoscope travels through the body cavities, image data obtained through imaging by the capsule endoscope inside the body cavities is sequentially transmitted by radio communication to the outside of the patient (in other words, subject) from an antenna such as a coil antenna. The antenna is arranged at the center of a back-end side of the capsule endoscope which is an opposite side from a side where an illuminating unit and an imaging unit are arranged. The transmitted image data is stored in a memory provided inside a receiver outside the subject. A doctor or a nurse can make diagnosis based on an image shown on a display according to the image data stored in the memory.

Conventionally, commonly-used capsule endoscopes of the above-described type are monocular capsule endoscopes. The monocular capsule endoscope takes only the image of an examined site located in front of the capsule endoscope, i.e., in an advancing direction thereof. In recent years, however, a pantoscopic capsule endoscope has been proposed for widening the field of view at the time of observation of, for example, an esophagus. The pantoscopic capsule endoscope takes images of a site behind itself as well as a site in front of itself along the advancing direction. As described in US Patent Application Laid-Open No. 2002-109774, for example, the pantoscopic capsule endoscope is configured to take images behind as well as ahead of a capsule-like casing along the advancing direction thereof in the body cavities, and a set of an illuminating unit such as a light emitting diode (LED) which illuminates an examined site and an imaging unit such as a charge-coupled device (CCD) which takes an image of an examined site is arranged in the capsule-like casing, one set at each of a front-end side and a back-end side.

In the pantoscopic capsule endoscope, one set of the illuminating unit and the imaging unit is arranged at each of the two ends of the capsule-like casing, and therefore, the antenna cannot be arranged at one end side of the capsule-like casing as in the monocular capsule endoscope. Therefore, the antenna must be arranged between or around components housed inside the capsule-like casing (for an example of the monocular capsule endoscope, see Japanese Patent Application Laid-Open No. 2001-112740, for example).

In the capsule-like casing, however, various components are housed, such as a substrate on which a conductive pattern, in particular, a wide ground pattern for grounding is formed, for example, and many electronic components mainly of metal. Therefore, when the antenna is arranged between or around the housed components, transmission waves from the antenna tend to be negatively affected, for example, distorted, shielded, or absorbed, by the conductor or metals. Then, it is difficult to obtain a desirable antenna characteristic, such as a wide directionality. Further, the arrangement of the antenna between or around the housed components necessitates the increased size of the capsule-like casing. Such necessity contradicts a demand for downsizing.

Further, even in the monocular capsule endoscope, the coil antenna, for example, is usually arranged at the center of the back-end side of the capsule-like casing and occupies a large space, and hampers a further downsizing of the capsule-like casing.

SUMMARY OF THE INVENTION

A body-insertable apparatus according to one aspect of the present invention includes a capsule-like casing that is formed in a capsule-like shape and includes a transparent imaging dome, an illuminating unit that is arranged in the capsule-like casing to illuminate an examined site of a subject through the imaging dome, an imaging unit that is arranged in the capsule-like casing to take an image of the examined site illuminated by the illuminating unit, an antenna that is arranged in the imaging dome at a position outside an imaging field of view of the imaging dome to transmit image information obtained through imaging by the imaging unit to an outside of the subject.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
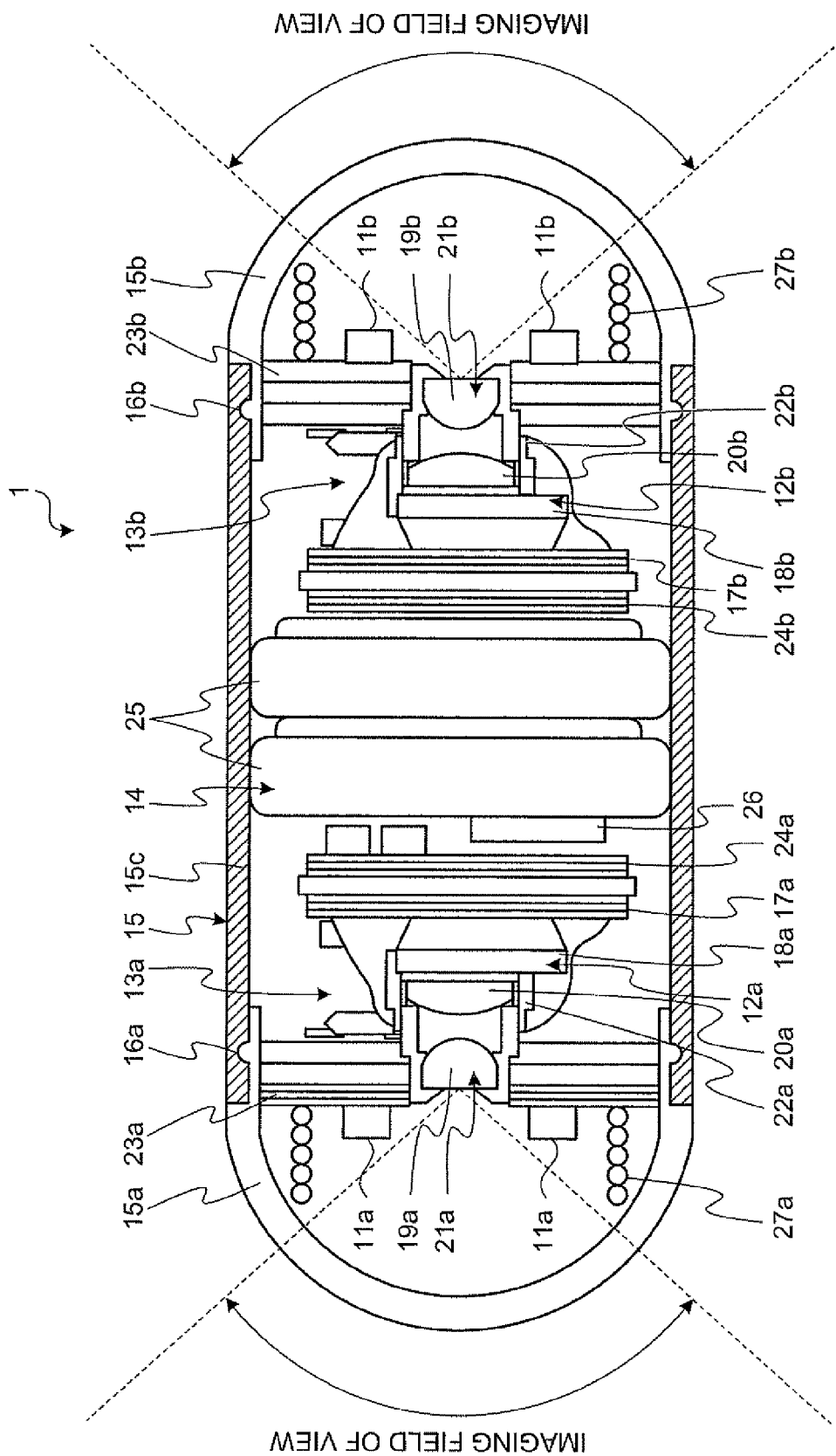
FIG. 1 is a sectional view of an internal structure of a capsule endoscope according to an embodiment.

An exemplary embodiment of a capsule endoscope which is a body-insertable apparatus according to the present invention will be described below with reference to the accompanying drawings. It should be noted that the present invention is not limited by the following embodiment. In the drawings, the same or corresponding portion will be denoted by the same reference character.

Figure 2:
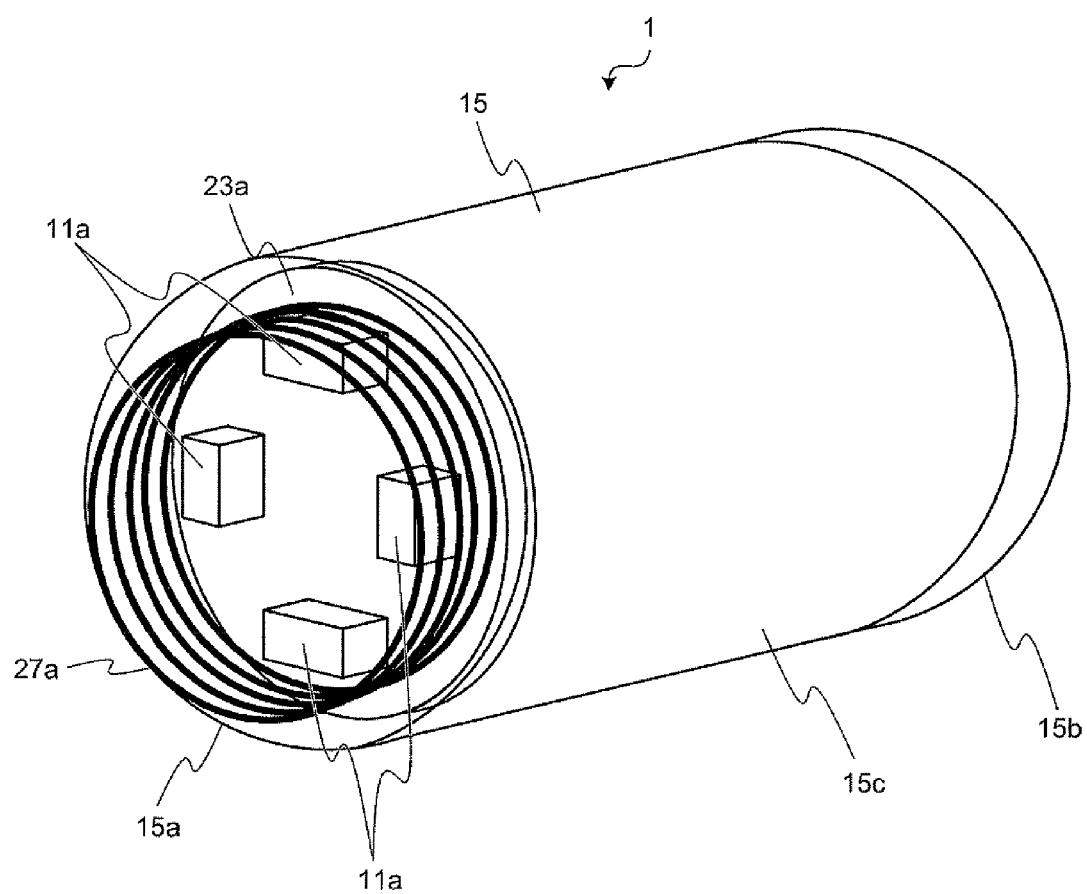
FIG. 2 is a schematic perspective view of the capsule endoscope shown in FIG. 1 with a part thereof removed.

FIG. 1 is a sectional view of an internal structure of a capsule endoscope according to an embodiment. FIG. 2 is a schematic perspective view of the capsule endoscope of the embodiment with a part thereof removed. A capsule endoscope 1 according to the embodiment is an application of a pantoscopic capsule endoscope which is inserted into a subject to take the image of an examined site and output the image by radio to the outside of the subject. The capsule endoscope 1 is configured with illuminating units 11a and 11b which illuminate examined sites of the subject and imaging units 12a and 12b which take the images of the examined sites. The illuminating unit 11a and the imaging unit 12a, and the illuminating unit 11b and the imaging unit 12b are respectively included in two imaging blocks 13a and 13b. The capsule endoscope 1 further includes a power supply unit 14 which supplies power to the above-mentioned units. These units are housed inside a capsule-like casing 15.

The capsule-like casing 15 is a capsule-like member including substantially semispherical, transparent imaging domes 15a and 15b and a cylindrical body 15c. The imaging dome 15a covers one end side of the imaging block 13a, whereas the imaging dome 15b covers one end side of the imaging block 13b. The body 15c has engaging portions 16a and 16b (grooves, for example) fitting with portions (flanges, for example) of the imaging domes 15a and 15b, and is engaged with the imaging domes 15a and 15b in a watertight manner. Inside the body 15c, the imaging blocks 13a and 13b are placed with the power supply unit 14 arranged therebetween. The capsule-like casing 15 is formed in such a size that the subject can swallow it from the mouth. The body 15c is made of a colored material which does not transmit visible light. The imaging dome of the body-insertable apparatus according to the present invention does not need to be a complete semisphere, and may be an oval or a partially cylindrical shape.

The imaging units 12a and 12b include imaging elements 18a and 18b and imaging lenses 21a and 21b, respectively. The imaging elements 18a and 18b are CCDs or complementary metal-oxide semiconductors (CMOS), for example, and take the image within a range illuminated by illumination light emitted from the illuminating units 11a and 11b, respectively. The imaging elements 18a and 18b are arranged respectively on disk-like imaging substrates 17a and 17b. The imaging lenses 21a and 21b include movable lenses 19a and 19b and fixed lenses 20a and 20b, respectively, to form an image on the imaging elements 18a and 18b, respectively. The movable lenses 19a and 19b and the fixed lenses 20a and 20b are supported by lens holders 22a and 22b, respectively.

The illuminating units 11a and 11b include, for example, light emitting diodes (LED). The illuminating units 11a and 11b are mounted on the surfaces of disk-like illuminating substrates 23a and 23b, respectively. The illuminating units 11a and 11b are arranged at four positions around optical axes of the imaging lenses 21a and 21b, respectively, above, below, to the right, and to the left of the optical axes. Further, in the imaging blocks 13a and 13b, signal processing/controlling units 24a and 24b are mounted on the back surface sides of the imaging substrates 17a and 17b, respectively, for processing and controlling each unit of the corresponding block. Further, the imaging substrates 17a and 17b are electrically connected to the illuminating substrates 23a and 23b, respectively, via a cable as appropriate.

The power supply unit 14 arranged between the imaging blocks 13a and 13b is configured, for example, with two button-type batteries 25 whose diameters are substantially equal to the inner diameter of the body 15c. As the battery 25, a silver oxide battery, a rechargeable battery, and a power-generating battery can be employed, for example. Further, a power supply substrate 26 is attached to one of the batteries 25. The power supply substrate 26 is electrically connected to each of the imaging substrate 17a, the illuminating substrate 23a, and the signal processing/controlling unit 24a via a cable or the like as appropriate. Further, the power supply substrate 26 is electrically connected to each of the imaging substrate 17b, the illuminating substrate 23b, and the signal processing/controlling unit 24b as appropriate via a cable or the like arranged outside the battery 25.

Further, the capsule endoscope 1 according to the embodiment includes antennas 27a and 27b which output image information obtained through imaging by the imaging units 12a and 12b by radio to a receiver outside the subject. Here, the antennas 27a and 27b are arranged inside the imaging domes 15a and 15b, respectively, outside the fields of view of the imaging units 12a and 12b in the imaging domes 15a and 15b. The antennas 27a and 27b are metal coil antennas mounted on the surfaces of the illuminating substrate 23a and 23b, respectively. The antennas 27a and 27b are subjected to antireflection treatment. For example, black coating is applied thereto. Modulating circuits are mounted on the back surface sides (inner surface sides) of the illuminating substrates 23a and 23b, respectively, to perform modulating process so that power supply can be performed near the antennas 27a and 27b.

After being swallowed by the subject, the capsule endoscope 1 with the above-described configuration illuminates examined site with the illuminating units 11a and 11b via the imaging domes 15a and 15b while imaging the examined sites with the imaging elements 18a and 18b via the imaging domes 15a and 15b. The signal processing/controlling units 24a and 24b perform necessary signal processing on the image information. The processed image information is output/transmitted to the receiver outside the subject via the corresponding antennas 27a and 27b by radio. Here, the outputs from the antennas 27a and 27b are set so that the receiver can distinguish the transmission waves from the antenna 27a from the transmission waves from the antenna 27b based on the difference in transmitting frequencies, or based on the modulation process performed thereon.

In the capsule endoscope 1 according to the embodiment, the transmitting antennas 27a and 27b are arranged inside the imaging domes 15a and 15b and outside the imaging fields of view of the imaging domes 15a and 15b, respectively. Thus, the antennas 27a and 27b can be arranged in an unused space in the capsule-like casing 15 without any disturbance to the imaging operations of the imaging units 12a and 12b, whereby further space saving and downsizing of the capsule-like casing 15 can be realized. Further, the antennas 27a and 27b are arranged outside the imaging fields of view, which form outwardly-expanding opening unobstructed by other units in the imaging domes 15a and 15b. Therefore, the transmission waves output from the antennas 27a and 27b are not negatively affected by other housed components such as the illuminating units 11a and 11b, the illuminating substrates 23a and 23b, and the imaging substrates 17a and 17b in the capsule-like casing 15, whereby a desirable antenna characteristic, such as a wide directionality, can be secured. Specifically, the directionality is further improved since the antennas 27a and 27b are provided one for each of the imaging blocks 13a and 13b.

Further, the antennas 27a and 27b are mounted on the surfaces of the illuminating substrates 23a and 23b which are electric components arranged at outermost positions in the capsule-like casing 15. Therefore, when the antennas 27a and 27b are arranged outside the imaging field of view of the imaging domes 15a and 15b, the mountability of the antennas 27a and 27b is not negatively affected. Further, though the antennas 27a and 27b, which are made basically of metal and arranged outside the imaging field of view, can negatively affect an imaging system by reflecting the illumination light, the antireflection treatment applied to the antennas 27a and 27b can prevent such inconvenience. Further, when the antennas 27a and 27b are arranged so as to abut on the illuminating units 11a and 11b, the antennas 27a and 27b can be positioned easily without the need of additional means such as adhesive.

Figure 3:
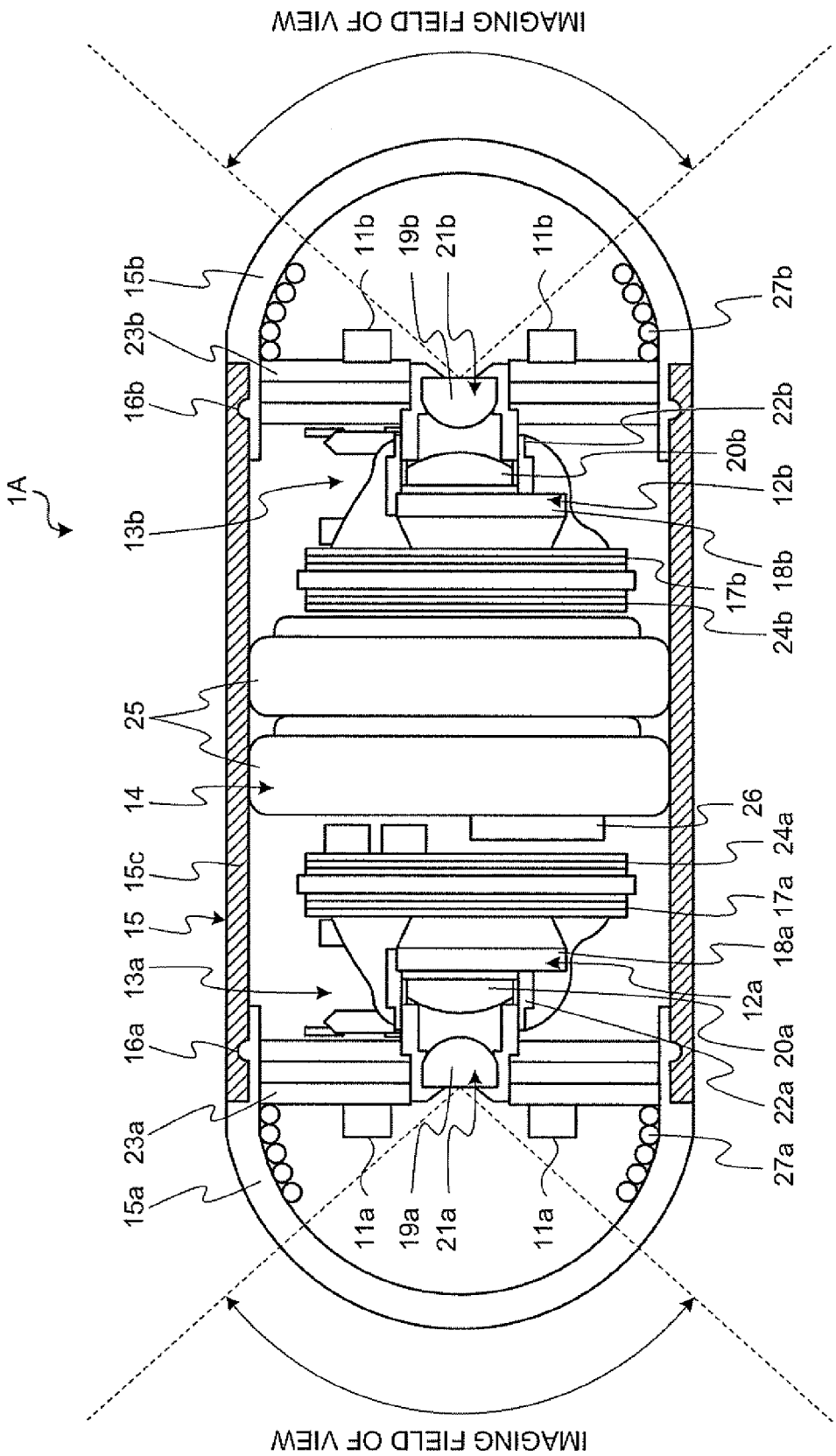
FIG. 3 is a sectional view of an internal structure of a capsule endoscope according to a first modification.

FIG. 3 is a sectional view of an internal structure of a capsule endoscope according to a first modification. A capsule endoscope 1A according to the first modification includes antennas 27a and 27b arranged along internal shapes of the substantially semi-spherical imaging domes 15a and 15b. More specifically, the antennas 27a and 27b are configured as metal coil antennas which have smoothly curved shapes conforming to the inner shapes of the imaging domes 15a and 15b.

Generally in the capsule endoscope, an optical system such as a fish-eye lens is mounted in the imaging units 12a and 12b to widen the imaging field of view, to 140°, for example, and the space which is outside the imaging field of view tends to decrease. However, when the antennas 27a and 27b are arranged along the inner shapes of the imaging domes 15a and 15b as in the first modification, the effective length of the antennas can be made longer within the limited space, which is advantageous for securing a favorable antenna characteristic.

Figure 4:
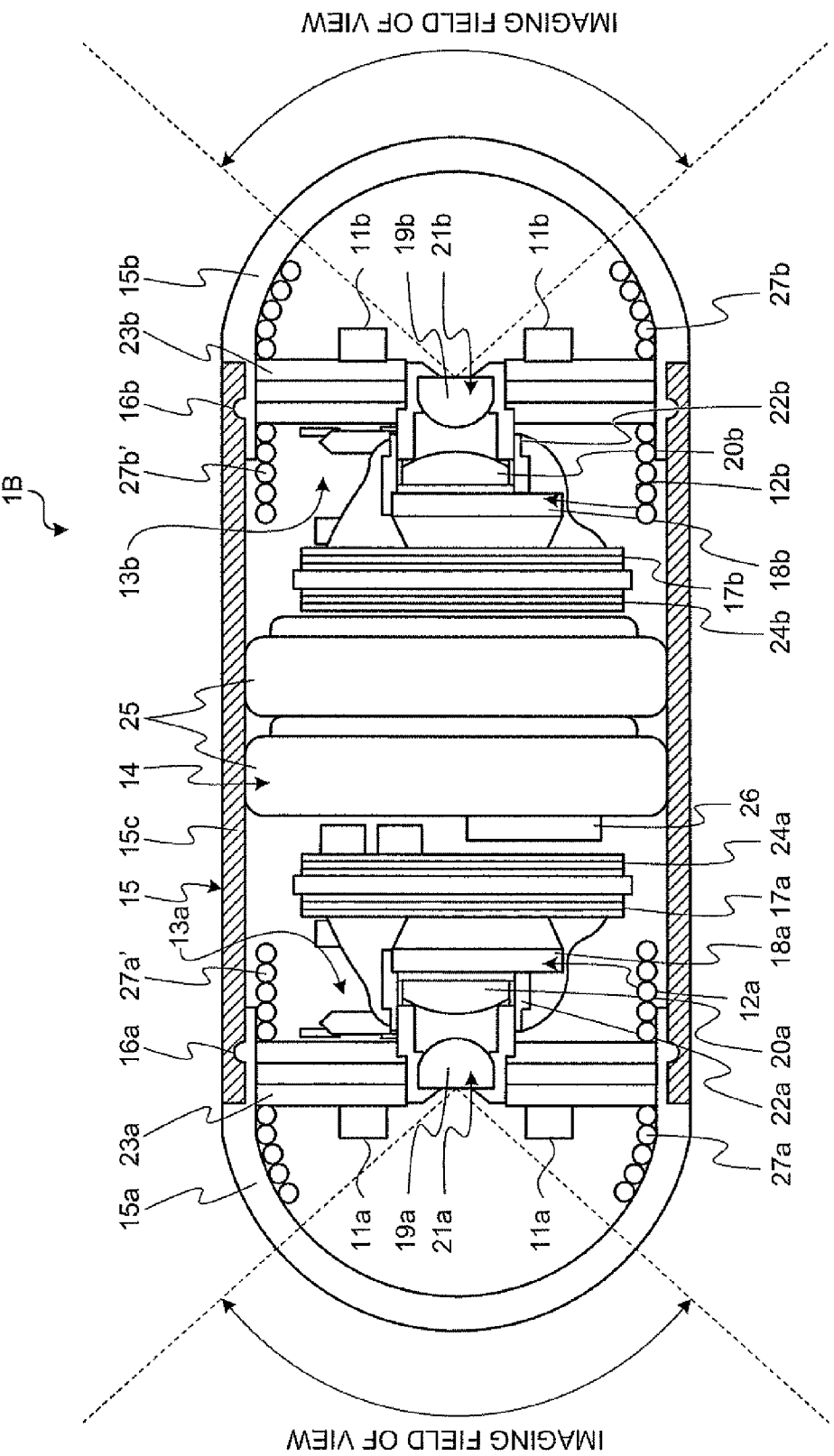
FIG. 4 is a sectional view of an internal structure of a capsule endoscope according to a second modification.

FIG. 4 is a sectional view of an inner structure of a capsule endoscope according to a second modification. The second modification takes into consideration a case where the arrangement of the antennas 27a and 27b shown in FIG. 3 cannot cover the sufficient, effective antenna length. In a capsule endoscope 1B according to the second modification, extension portions 27a' and 27b' are additionally mounted on the back surface sides of the illuminating substrates 23a and 23b by necessary lengths as the extensions of the antennas 27a and 27b as shown in FIG. 4.

Figure 5:
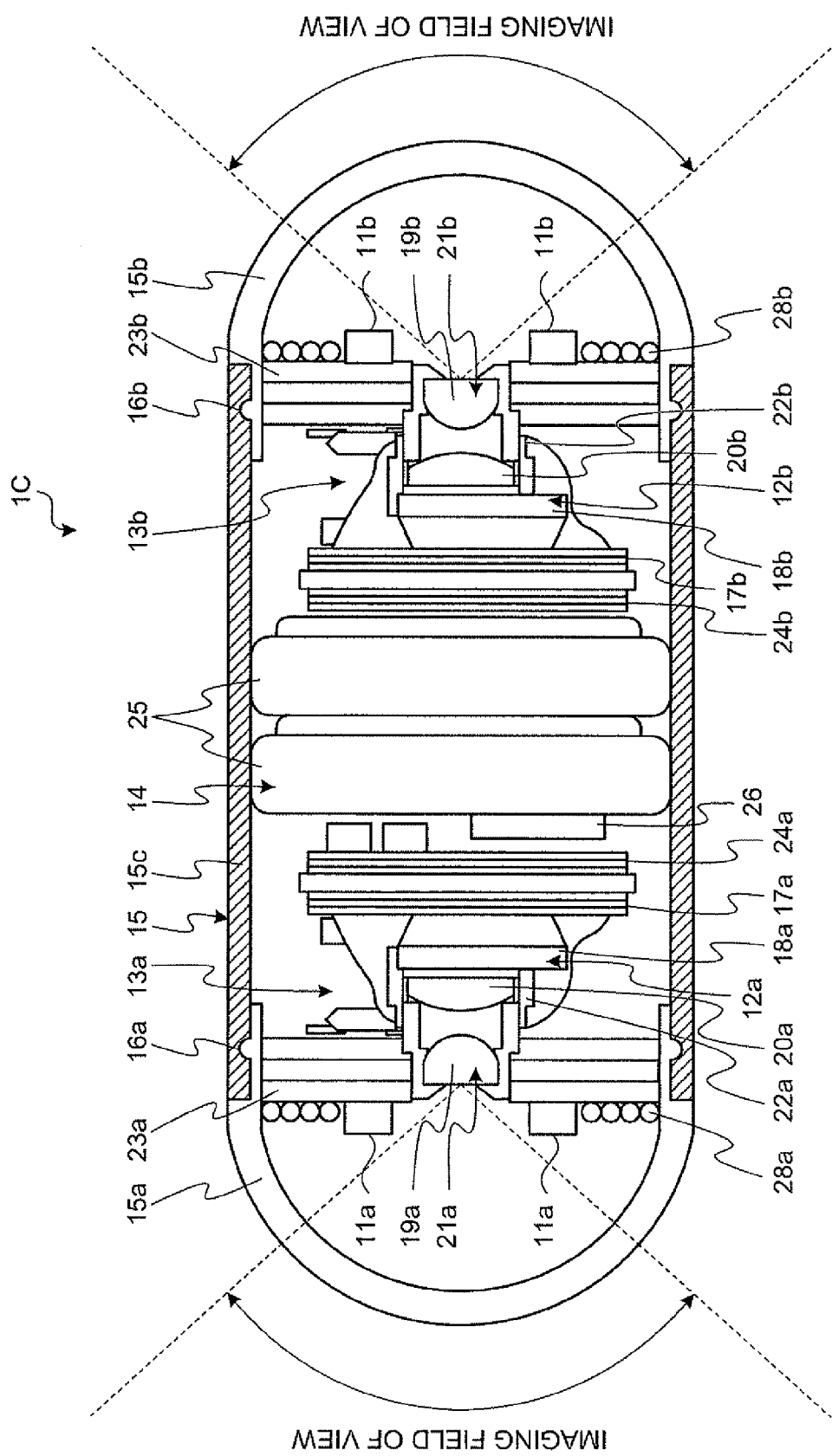
FIG. 5 is a sectional view of an internal structure of a capsule endoscope according to a third modification.

FIG. 5 is a sectional view of an internal structure of a capsule endoscope according to a third modification. A capsule endoscope 1C according to the third modification includes antennas 28a and 28b formed as planar coil patterns on the surfaces of the illuminating substrates 23a and 23b instead of the metal coil antennas 27a and 27b. The antennas 28a and 28b formed as planar coil patterns do not protrude much in the axial direction of the capsule-like casing 15. Therefore, the antennas 28a and 28b can easily be arranged outside the imaging field of view even when there is only a small useable space (i.e., unused space) outside the imaging field of view. The planar coil patterns may be formed on the back surface sides of the illuminating substrates 23a and 23b.

When the antennas 28a and 28b are formed as planar coil patterns, it is desirable that the antennas 28a and 28b be formed similarly to wiring patterns of the illuminating substrates formed through high-precision etching in a fabrication process of the illuminating substrates 23a and 23b. It is also possible, however, to form planar antennas from the metal coil antennas employed in the capsule endoscopes 1A and 1B of the first and the second modifications and mount them on the illuminating substrates 23a and 23b.

Figure 6:
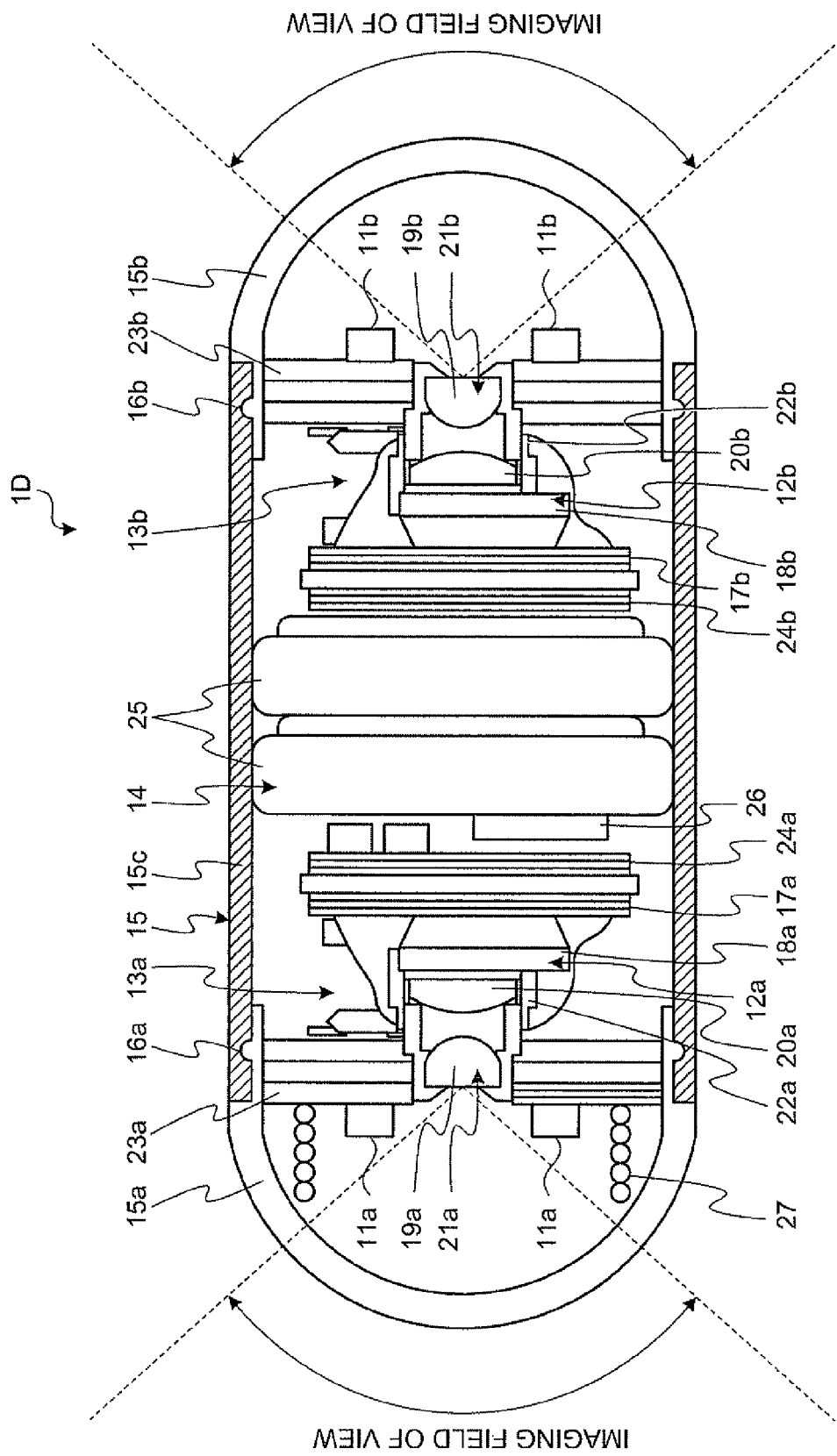
FIG. 6 is a sectional view of an internal structure of a capsule endoscope according to a fourth modification.

FIG. 6 is a sectional view of an internal structure of a capsule endoscope according to a fourth modification. In the pantoscopic capsule endoscopes of the embodiment and the modifications described above, one antenna is arranged in each of the imaging blocks 13a and 13b. In a capsule endoscope 1D according to a fourth modification, one antenna 27 is arranged to be shared by the imaging units 12a and 12b. The antenna 27 is arranged, for example, at the side of the imaging dome 15a. The single antenna 27 transmits/outputs the image information obtained through imaging by the imaging units 12a and 12b to the outside of the subject in a time-divisional manner so that the antenna 27 can process the outputs of both the imaging units 12a and 12b.

In the above, the fourth modification is explained as an application of the antenna structure of the capsule endoscope 1 of the embodiment. However, the antenna structures of the capsule endoscopes 1A to 1C of the first to the third modifications are similarly applicable.

Figure 7:
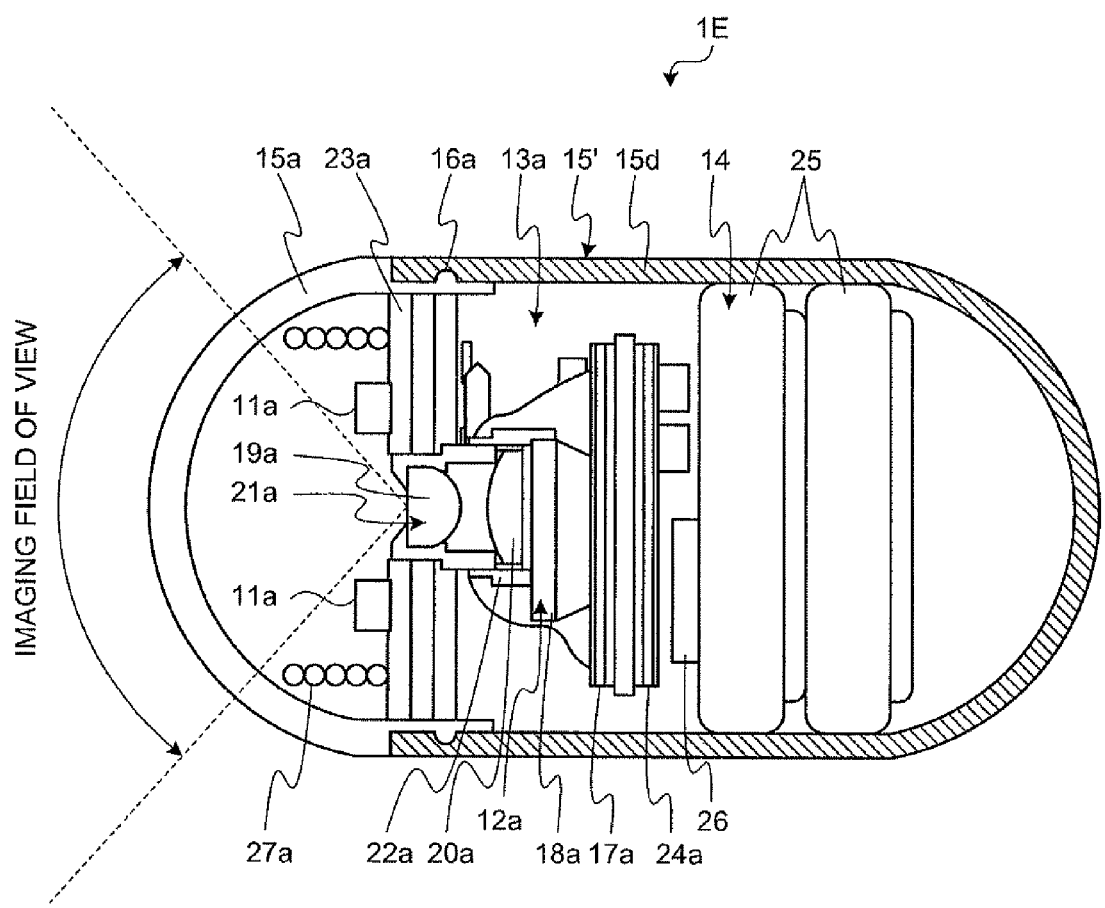
FIG. 7 is a sectional view of an internal structure of a capsule endoscope according to a fifth modification.

FIG. 7 is a sectional view of an internal structure of a capsule endoscope according to a fifth modification. While the embodiment and the modifications described above relate to the application of a pantoscopic capsule endoscope, a capsule endoscope 1E according to the fifth modification is an application of a monocular capsule endoscope. A capsule-like casing 15' is configured as a combination of an imaging dome 15a and a bottomed body 15d. There is no components corresponding to those arranged at the side of the imaging block 13b, and only the components corresponding to those arranged at the side of the imaging block 13a are provided.

Similarly to the other capsule endoscopes described above, in the monocular capsule endoscope 1E, the antenna 27a is arranged in an unused space in the imaging dome 15a and outside the imaging field of view of the imaging dome 15a, whereby it is not necessary to arrange the antenna at the bottom center of the bottomed body 15d. Thus, the capsule-like casing 15' can be further downsized. Further, if the capsule-like casing 15' has a similar size as the conventional casing, the space at the bottom of the bottomed body 15d can be effectively utilized for mounting a signal processor and other functional units, or for mounting the larger battery 25 to increase a battery capacity. Still further, since the antenna is not arranged in the bottomed body 15d, other components can easily be arranged and embedded in the bottomed body 15d.

Though the fifth modification is explained as an application of the antenna structure of the capsule endoscope 1 of the embodiment, the antenna structures of the capsule endoscopes 1A to 1C of the first to the third modifications are also similarly applicable.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body-insertable apparatus comprising:
a capsule-like casing that is formed in a capsule-like shape and includes a transparent imaging dome;
an illuminating unit that is arranged in the capsule-like casing to illuminate an examined site of a subject through the imaging dome;
an imaging unit that is arranged in the capsule-like casing to take an image of the examined site illuminated by the illuminating unit; and
an antenna that is arranged in the imaging dome at a position outside an imaging field of view of the imaging dome to transmit image information obtained through imaging by the imaging unit to an outside of the subject;

wherein the antenna is subjected to an antireflection treatment.

2. The body-insertable apparatus according to claim 1, wherein
the antenna is arranged on a front surface side of an illuminating substrate on which the illuminating unit is arranged.

3. The body-insertable apparatus according to claim 1, wherein
the antenna is arranged closer to an outer circumference of the capsule-like casing than the illuminating unit which is arranged on the illuminating substrate.

4. The body-insertable apparatus according to claim 2, wherein
the antenna is formed as a pattern on the front surface side of the illuminating substrate.

5. The body-insertable apparatus according to claim 2, wherein
the antenna is mounted on the front surface side of the illuminating substrate.

6. The body-insertable apparatus according to claim 1, wherein
the antenna is a metal coil antenna.

7. The body-insertable apparatus according to claim 5, wherein
the antenna has an extension which is mounted on a back surface side of the illuminating substrate.

8. The body-insertable apparatus according to claim 1, wherein
the antenna is arranged along a shape of an inner surface of the imaging dome.

9. The body-insertable apparatus according to claim 3, wherein
the antenna is arranged in contact with the illuminating unit.

10. The body-insertable apparatus according to claim 1, wherein
the capsule-like casing has a plurality of the imaging domes,
the illuminating unit and the imaging unit are provided in each of the imaging domes, and
the antenna is arranged in at least one of the imaging domes.

* * * * *